US012691104B2

(12) United States Patent
Stuelsatz et al.

(10) Patent No.: US 12,691,104 B2
(45) **Date of Patent: *Jul. 28, 2026**

(54) COMPOSITIONS CONTAINING NICOTINAMIDE AND VITAMIN B6 AND METHODS OF USING SUCH COMPOSITIONS FOR TREATING SARCOPENIA AND FRAILTY

(71) Applicant: SOCIETE DES PRODUITS NESTLE S.A., Vevey (CH)

(72) Inventors: Pascal Stuelsatz, Crissier (CH); Jerome Feige, Crissier (CH); Joris Michaud, Lausanne (CH); Eugenia Linda Migliavacca, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 512 days.

This patent is subject to a terminal disclaimer.

(21) Appl. No.: 18/250,874

(22) PCT Filed: Oct. 29, 2021

(86) PCT No.: PCT/EP2021/080111
§ 371 (c)(1),
(2) Date: Apr. 27, 2023

(87) PCT Pub. No.: WO2022/090458
PCT Pub. Date: May 5, 2022

(65) Prior Publication Data
US 2023/0390262 A1      Dec. 7, 2023

(30) Foreign Application Priority Data

Oct. 30, 2020     (EP) .................................... 20204865

(51) Int. Cl.
*C07D 213/82*       (2006.01)
*A61K 31/4415*    (2006.01)
*A61K 31/455*      (2006.01)
*A61P 21/00*        (2006.01)
*C07D 213/67*       (2006.01)

(52) U.S. Cl.
CPC ........ *A61K 31/4415* (2013.01); *A61K 31/455* (2013.01); *A61P 21/00* (2018.01)

(58) Field of Classification Search
CPC ................ C07D 213/82; C07D 213/67; A61K 31/4415; A61K 31/455; A61P 21/00
See application file for complete search history.

(56) References Cited

U.S. PATENT DOCUMENTS

| | | | |
|---|---|---|---|
| 2012/0288588 A1 | 11/2012 | Barron | |
| 2023/0390263 A1* | 12/2023 | Stuelsatz | ............ A61K 31/4415 |
| 2023/0390264 A1* | 12/2023 | Stuelsatz | ................ A61P 21/00 |
| 2023/0398104 A1* | 12/2023 | Stuelsatz | ............ A61K 31/4415 |
| 2025/0186418 A1* | 6/2025 | Stuelsatz | ................ A61P 21/00 |

FOREIGN PATENT DOCUMENTS

| | | |
|---|---|---|
| AT | 513274 | 3/2014 |
| CN | 101669938 A | 3/2010 |
| CN | 102688201 A | 9/2012 |
| CN | 107114800 | 9/2017 |
| CN | 109077302 A | 12/2018 |
| CN | 109562104 A | 4/2019 |
| CN | 109588709 | 4/2019 |
| JP | 2006503896 A | 2/2006 |
| JP | 2023523556 A | 6/2023 |
| WO | 2005102301 | 11/2005 |
| WO | 2013056048 | 4/2013 |
| WO | 2018221526 A1 | 12/2018 |
| WO | 2021004919 | 1/2021 |

OTHER PUBLICATIONS

Guo et al. "Nicotinamide protects against skeletal muscle atrophy in streptozotocin-induced diabetic mice" Archives of Physiology and Biochemistry, 2019, vol. 125, No. 5, pp. 470-477.

Suidasari et al. "Dietary vitamin B6 modulates the gene expression of myokines, Nrf2-related factors, myogenin and HSP60 in the skeletal muscle of rats" Experimental and Therapeutic Medicine, 2017, vol. 14, pp. 3239-3246.

Japanese Office Action for Appl No. 2023-518434 dated Aug. 12, 2025, 6 pages.

Chinese Office Action for Appl No. 202180061952.2 dated Dec. 19, 2025, 7 pages.

* cited by examiner

*Primary Examiner* — Brenda L Coleman
(74) *Attorney, Agent, or Firm* — K&L Gates LLP

(57)           ABSTRACT

A composition contains Nicotinamide and pyridoxine. The composition may be an oral nutritional composition, for example a nutritional supplement, an oral nutritional supplement, a food product, a food for special medical purpose (FSMP). The composition can be administered to an individual in need thereof orally or intravenously for preventing and/or treating sarcopenia, physical frailty, a loss of and/or improving skeletal muscle mass, lean muscle mass, skeletal muscle strength and/or skeletal muscle function.

16 Claims, 8 Drawing Sheets

A

B

A

B

A

B

A

B

A    Muscle Stem Cell amplification

B    Muscle Stem Cell commitment

A     Muscle Stem Cell Amplification

B     Muscle Stem Cell commitment

COMPOSITIONS CONTAINING NICOTINAMIDE AND VITAMIN B6 AND METHODS OF USING SUCH COMPOSITIONS FOR TREATING SARCOPENIA AND FRAILTY

CROSS REFERENCE TO RELATED APPLICATIONS

The present application is a National Stage of International Application No. PCT/EP2021/080111, filed on Oct. 29, 2021, which claims priority to European Patent Application No. 20204865.8, filed on Oct. 30, 2020, the entire contents of which are being incorporated herein by reference.

TECHNICAL FIELD

The present disclosure generally relates to compositions containing Nicotinamide and pyridoxine and also relates to methods of preparing and using such compositions. The composition may be an oral nutritional composition, for example a nutritional supplement, an oral nutritional supplement, a food product, a food for special medical purpose (FSMP). The composition can be administered to an individual in need thereof orally or intravenously for preventing and/or treating sarcopenia, a loss of and/or improving skeletal muscle mass, lean muscle mass, skeletal muscle strength and/or skeletal muscle function.

BACKGROUND

Sarcopenia, or the decline of skeletal muscle tissue with age, is one of the most important causes of functional decline and loss of independence in older adults. Sarcopenia has been defined as an age related, involuntary loss of skeletal muscle mass and strength. Beginning as early as the 4th decade of life, evidence suggests that skeletal muscle mass and skeletal muscle strength decline in a linear fashion, with up to 50% of mass being lost by the 8th decade of life. Given that muscle mass accounts for about 40% of body mass, pathological changes to this important metabolically active tissue can have profound consequences on the older adult. The consequences of sarcopenia are often severe in older adults, as the strength and functional declines associated with sarcopenia can in turn contribute to a number of adverse health outcomes, including loss of function, disability, frailty and potentially loss of autonomy. Sarcopenia is also associated with acute and chronic disease states, increased insulin resistance, fatigue, falls, and mortality. Of the chronic disease states, sarcopenia has been associated with rheumatologic conditions, especially rheumatoid arthritis (RA) in women, among many other diseases.

Sarcopenia is a multi-factorial syndrome which associates with pathophysiological changes, such as impaired neuro-muscular transition, altered excitation/contraction coupling, impaired regenerative capacity linked to stem cell exhaustion, defects of mitochondrial and energy metabolism in myofibers, and marbling of skeletal muscle with fat and fibrosis. The aetiology of this syndrome is therefore complex and poorly understood, but low physical activity, hormonal decline in anabolic hormones (e.g. androgens and IGF-1), and malnutrition and/or nutritional deficiencies play an important role.

The physiological and morphological changes in skeletal muscle with advancing age are characterized by overall declines in size and number of skeletal muscle fibers, mainly the type 2 or fast-twitch muscle fibers, and a marked infiltration of fibrous and adipose tissue into the skeletal muscle.

Although aging-related biological changes clearly drive sarcopenia, it is increasingly clear that other factors such as inactivity due to injuries or sickness, obesity and fat infiltration into skeletal muscle also cause lower muscle quality and an accelerated loss of lean body mass.

Reduced physical activity is thought to increase the likelihood of sarcopenia and therefore increased exercise will likely be beneficial in combating the condition. Indeed, resistance exercise is associated with increased synthesis of proteins in skeletal muscle. However, exercise as a treatment often suffers from poor patient compliance.

The current gold standard to counteract muscle wasting is physiotherapy. There are currently no approved drugs to treat muscle-wasting diseases. Anabolic drugs (SARMs, ghrelin agonists, myostatin inhibitors) are in Ph.II or Ph.III clinical trials. Current nutritional solutions largely rely on high protein content in order to boost muscle anabolism but have limited efficacy and are not proprietary and poorly differentiated.

Muscle stem cells have been widely investigated in muscle plasticity during health and disease both in preclinical models and in humans. Muscle stem cell function and regeneration is a potential target to enhance muscle healing both in healthy and diseased conditions. However, there are currently no product on the market targeting muscle stem cells, and researches for therapeutic approaches have been focused on using drugs, and are for the most part still in a preclinical stage. Nevertheless, it appears evident that the nutritional status can affect muscle stem cells and interest for nutritional interventions to target muscle stem cells has been recently growing. So far, most studies have only tested a limited number of nutrients with known potential beneficial effect, and there is a need for larger scale screenings aiming at identifying novel nutritional compounds.

The present inventors identified that there is an increasing demand for a solution for preventing and/or treating the loss of skeletal muscle mass, lean muscle mass, the skeletal muscle strength and/or the skeletal muscle function in an individual in need thereof, for example, treating sarcopenia in elderly adults; and an increasing demand for improving the skeletal muscle mass, the skeleton lean muscle mass, the skeletal muscle strength and/or the skeletal muscle function in an individual in need thereof.

SUMMARY

As set forth in the experimental examples disclosed later herein, the present inventors surprisingly identified Nicotinamide as an enhancer of both amplification and commitment of muscle stem cells and vitamin B6 as an enhancer of their commitment. The present inventors also surprisingly found that the effect of Nicotinamide and vitamin B6 (e.g. pyridoxine) when tested alone, was potentiated when cells were treated with a combination of these two compounds. This synergistic effect that is shown and described in FIG. 3 might be explained by the fact that Nicotinamide and vitamin B6 act differently on the muscle stem cells with Nicotinamide increasing mainly the amplification step (Pax7 cells) while vitamin B6 targeting specifically the commitment step (MyoD cells). This effect has been shown specific to B6 compared with other B vitamins (e.g B9). A composition comprising the combination was advantageous in maintaining stem cell function. In particular, a combination of Nicotinamide and vitamin B6 (e.g. pyridoxine) particularly at specific concentrations and/or specific ratios thereof, unexpectedly showed a statistically significant synergistic association between the Nicotinamide and pyridoxine and the increase in muscle regeneration by promoting muscle stem cell function, thus suggesting an effect of these nutrients on preventing and/or treating the loss of and/or improving skeletal muscle mass, skeleton lean muscle mass, skeletal muscle strength and/or skeletal muscle function in an individual in need thereof, especially for treating sarcopenia in an elderly adult. In an aspect of the present disclosure, a composition comprises a combination of Nicotinamide and Vitamin B6 (e.g. pyridoxine) preferably an amount of the combination that is therapeutically effective for at least one of the physiological benefits disclosed herein.

In an embodiment, the composition comprises vitamin B6 in an amount of a daily dosage of 1.0-600 mg of vitamin B6/day, for example 1.0-200.0 mg of vitamin B6/day, for example 1.0-25.0 mg of vitamin B6/day, for example 1.0-15.0 mg of vitamin B6/day, for example 1.0-10 mg of vitamin B6/day, for example 1.0-7.0 mg of vitamin B6/day.

In an embodiment, the composition comprises Nicotinamide in an amount of about 1 mg/day to about 3000 mg/day, for example about 10 mg/day to about 2000 mg/day, for example about 500 mg/day to about 1000 mg/day.

In an embodiment, the composition comprises the Vitamin B6 in an amount of 10.0 to 20.0 mg vitamin B6 per day and/or the Nicotinamide is administered in an amount of about 500 mg to about 1000 mg Nicotinamide per day.

However, in any given case, the amount of compound administered will depend on such factors as the solubility of the active component, the formulation used, subject condition (such as weight), and/or the route of administration. For example, the daily doses of Vitamin B6 or Nicotinamide disclosed above are non-limiting and, in some embodiments, may be different; in particular, the compositions disclosed herein can be utilized as an acute care food for special medical purposes (FSMP).

In an embodiment, the composition is in a form of a solid powder, a powdered stick, a capsule or a solution. The composition can be a food supplement, a medical food, a nutritional composition, for example an oral nutritional composition.

In another aspect of the present disclosure, a method of preparing the composition is provided. The method can comprise combining Vitamin B6 (e.g. pyridoxine) and Nicotinamide, and preferably an amount of the resultant combination that is therapeutically effective for at least one of the physiological benefits disclosed herein.

In another aspect of the present disclosure, a nutritional supplement comprises a therapeutically effective amount of any of the compositions disclosed herein. In an embodiment, the nutritional supplement is an oral nutritional supplement (ONS). The nutritional supplement can be in a form of a solid powder, a powdered stick, a capsule, or a solution. In an embodiment, the nutritional supplement comprises vitamin B6 in a daily dosage of 1.0-600 mg vitamin B6, for example 1.0-200 mg vitamin B6, for example 1.0-25.0 mg vitamin B6. The nutritional supplement comprises Nicotinamide in a total daily dosage about 1 mg/day to about 3000 mg/day, preferably about 10 mg/day to about 2000 mg/day, more preferably from 500 mg/day to about 1000 mg/day.

In another aspect of the present disclosure, a food product comprises any of the compositions disclosed herein. In an embodiment, the food product is a food for special purpose (FSMP). The food product can comprise vitamin B6 in a daily dosage of 1.0-600 mg vitamin B6, for example 1.0-200 mg vitamin B6, for example 1.0-25.0 mg vitamin B6. The nutritional supplement comprises Nicotinamide in a total daily dosage about 1 mg/day to about 3000 mg/day, preferably about 10 mg/day to about 2000 mg/day, more preferably from 500 mg/day to about 1000 mg/day.

In an embodiment, the food product further comprises one or more additional ingredients, for example a lipid, a protein, a carbohydrate, a vitamin, a mineral, or any combination thereof.

In another aspect of the present disclosure, a kit comprises a therapeutically effective amount of any of the compositions disclosed herein. In an embodiment, the kit is configured for oral administration of the composition. For example, the kit can comprise at least two capsules in which a first capsule comprises the vitamin B6 and a second capsule comprises Nicotinamide. In an embodiment, the kit comprises vitamin B6 in the first capsule in a daily dosage of 1.0-600 mg vitamin B6, for example 1.0-200 mg vitamin B6, for example 1.0-25.0 mg vitamin B6. The nutritional supplement comprises Nicotinamide in a total daily dosage about 1 mg/day to about 3000 mg/day, preferably about 10 mg/day to about 2000 mg/day, more preferably from 500 mg/day to about 1000 mg/day.

In another aspect of the present disclosure, a method of preventing and/or treating a loss of and/or improving skeletal muscle mass, skeleton lean muscle mass, skeletal muscle grip strength and/or skeletal muscle function is provided. The method comprises administering to an individual in need thereof a therapeutically effective amount of a combination of vitamin B6 and Nicotinamide. In an embodiment, the administration is by oral administration. In another embodiment, the administration is by intravenous administration.

The present invention also relates to a method for treating or preventing sarcopenia and/or restoring and/or correcting deficiencies of nutrients in a subject. In one embodiment, the subject is identified as having sarcopenia or is at increased risk of developing sarcopenia.

In one embodiment, the subject is a human subject.

In one embodiment, the human subject is an older adult. In one embodiment, the human subject is elderly.

In one embodiment, the subject is a companion animal, preferably a dog.

Human Skeletal Muscle Myoblasts were purchased from Lonza (https://bioscience.lonza.com). These cells were isolated from the upper arm or leg muscle tissue of normal donors and used after the second passage. Several donors were tested to ensure cell viability and purity before selecting the final donors, which are a 20-year-old Caucasian female (refer thereafter as Donor 1), a 36-year-old Caucasian female (refer thereafter as Donor 2) and a 18-year-old Caucasian male (refer thereafter as Donor 3). Human primary myoblasts were seeded in 384 well plates at a density of 1'000 cells per well in skeletal muscle growth medium (SKM-M, AMSbio). For treatment, compounds were directly added to the myoblast cultures 16 hours after initial plating.

All cultures were then grown for 96 hours. Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification. *, , *, **** indicates difference from the control, One-way ANOVA, with p<0.05, p<0.01, p<0.001, p<0.0001, respectively. Data are presented as Mean+/—SEM.

Figure 1:
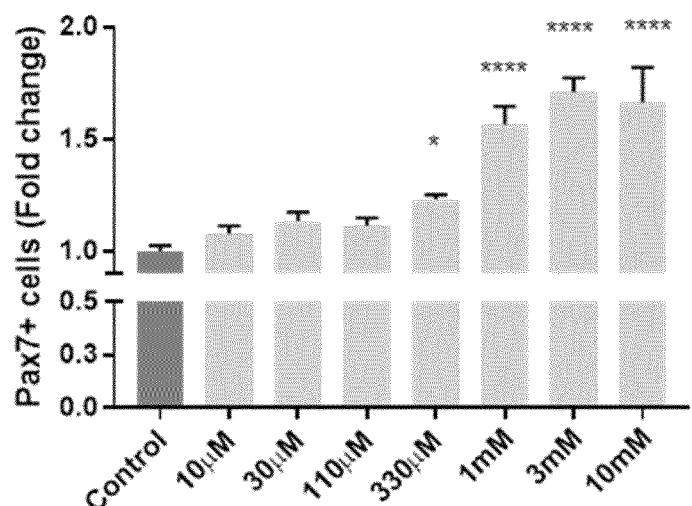
FIGS. 1 to 5—Myogenic amplification and commitment of muscle stem cells
Figure 1:
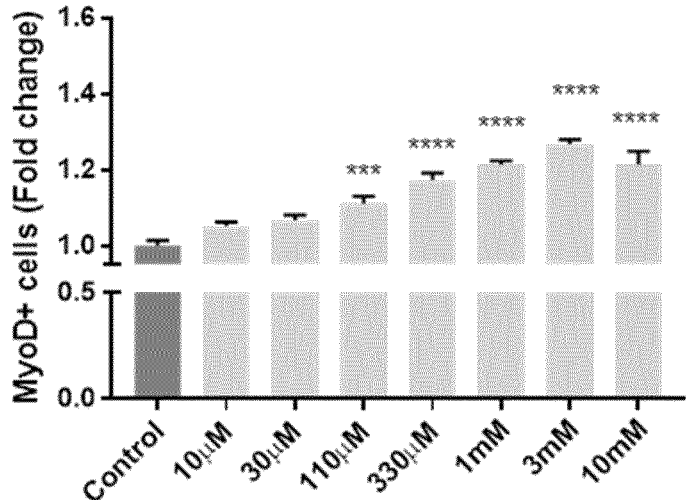

FIG. 1: In vitro dose response of Nicotinamide. Data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 1A represents the proportion of Pax7+ cells and FIG. 1B represents the proportion of MyoD+ cells.

Figure 2:
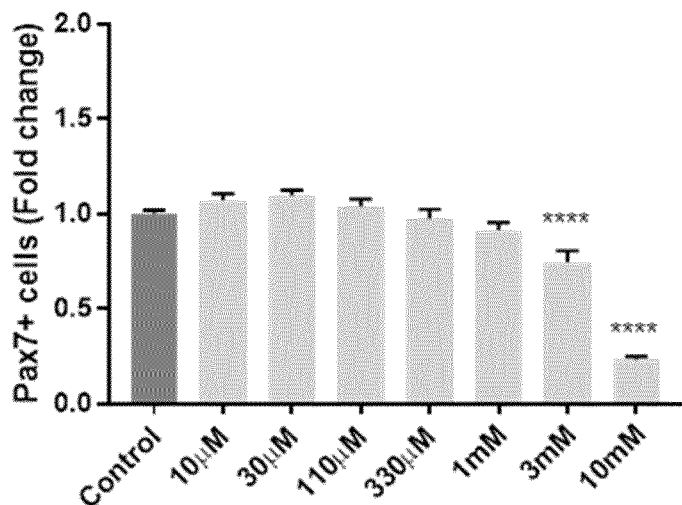
Figure 2:
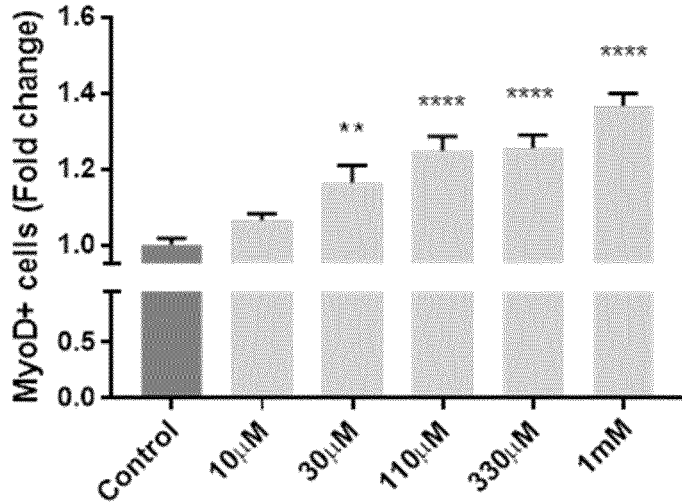

FIG. 2: In vitro dose response of Pyridoxine (B6). Data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 2A represents the proportion of Pax7+ cells and FIG. 2B represents the proportion of MyoD+ cells.

Figure 3:
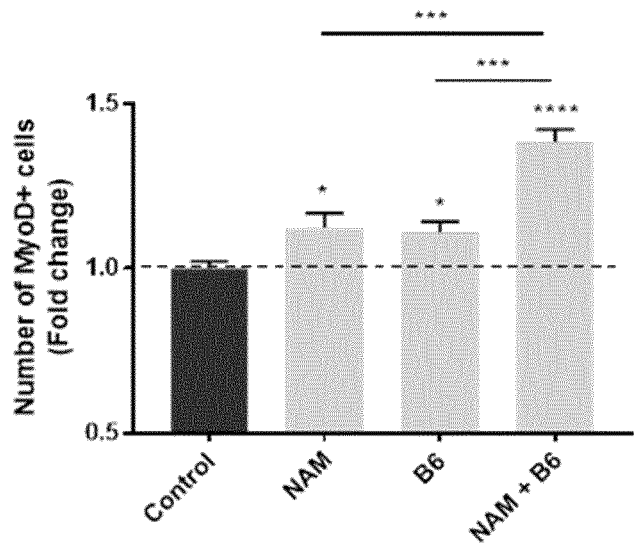
Figure 3:
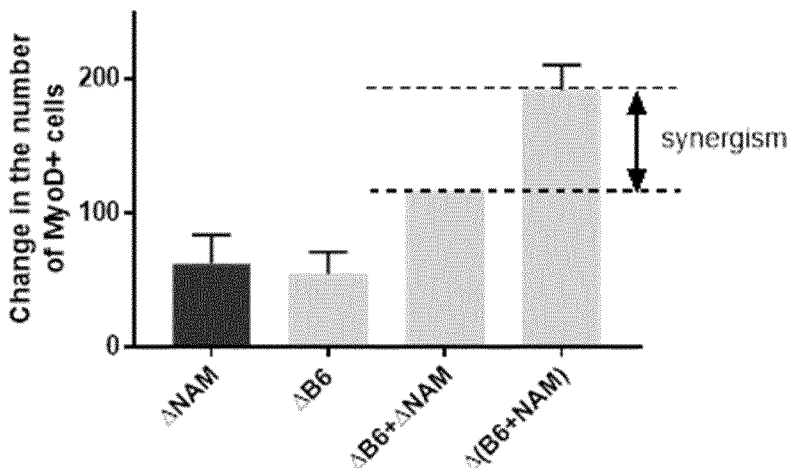

FIG. 3: Synergistic effect of Nicotinamide (NAM) and pyridoxine (B6). The effect of nicotinamide and pyridoxine alone or combined on the MyoD+ cells was assessed on Human primary myoblasts from donor 3. For each condition, the number of MyoD+ cells was normalized to the number of MyoD+ cells in the control condition (DMSO 1%). FIG. 3A represents the number of MyoD+ cells normalized to the control condition. FIG. 3B represents the increase in MyoD+ cell number compared to the control condition (DMSO 1%). $\Delta$B6 or $\Delta$NAM refers to the change from the control condition with B6 or NAM treatment, respectively. $\Delta$B6+$\Delta$NAM refers to the theoretical sum of the effects of B6 and NAM measured separately. $\Delta$(B6+NAM) refers to the experimental effects of a combined treatment with B6 and NAM. A statistically significant synergistic effect between the nicotinamide and pyridoxine has been observed by applying a linear regression model (interaction term, p=0.05).

Figure 4:
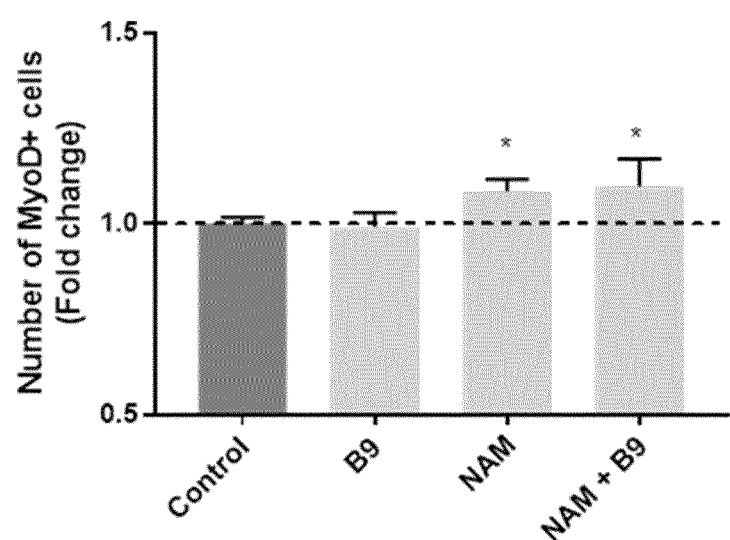
Figure 4:
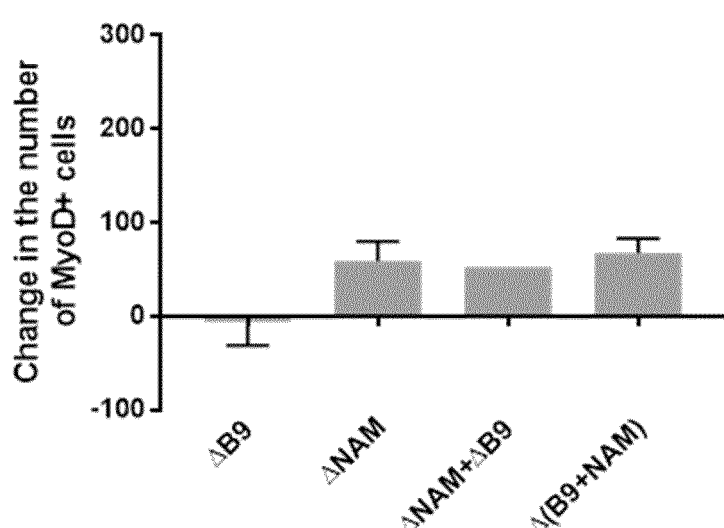

FIG. 4 Combination of Nicotinamide (NAM) with vitamin B9. The effect of nicotinamide and vitamin B9 alone or combined on the MyoD+ cells was assessed on Human primary myoblasts from donor 3. For each condition, the number of MyoD+ cells was normalized to the number of MyoD+ cells in the control condition (DMSO 1%). FIG. 4A represents the number of MyoD+ cells normalized to the control condition. FIG. 4B represents the increase in MyoD+ cell number compared to the control condition (DMSO 1%). $\Delta$B9 or $\Delta$NAM refers to the change from the control condition with B9 or NAM treatment, respectively. $\Delta$B9+$\Delta$NAM refers to the theoretical sum of the effects of B9 and NAM measured separately. $\Delta$(B9+NAM) refers to the experimental effects of a combined treatment with B9 and NAM.

Figure 5:
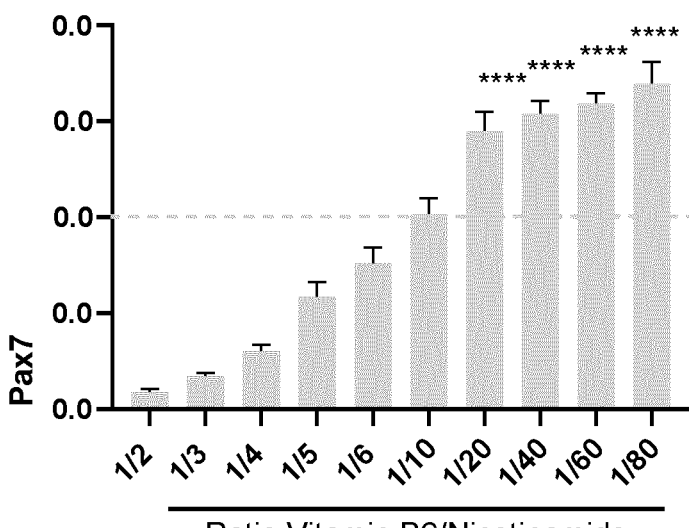

FIG. 5 represents the number of Pax7+ cells for different ratios between Pyridoxine and Nicotinamide (ratio Vitamin B6/NAM).

Figure 6:
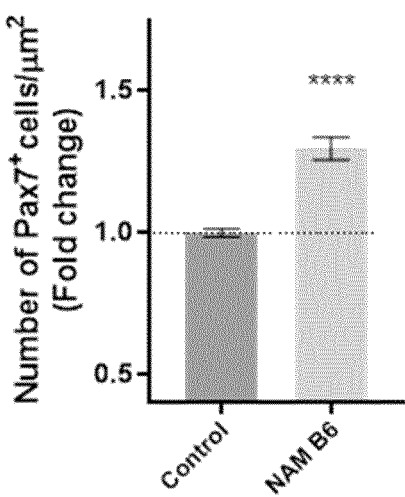
Figure 6:
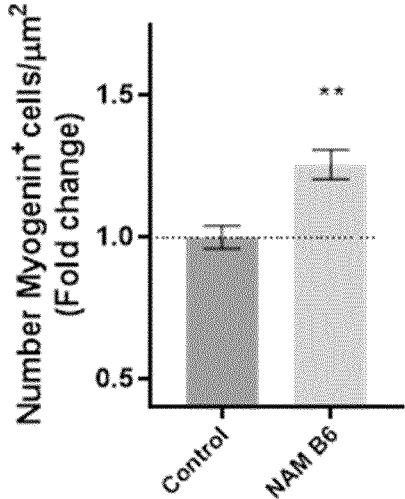
Figure 7:
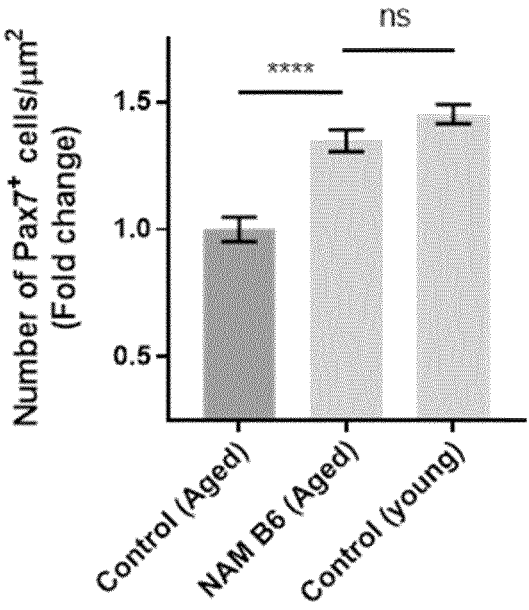
Figure 7:
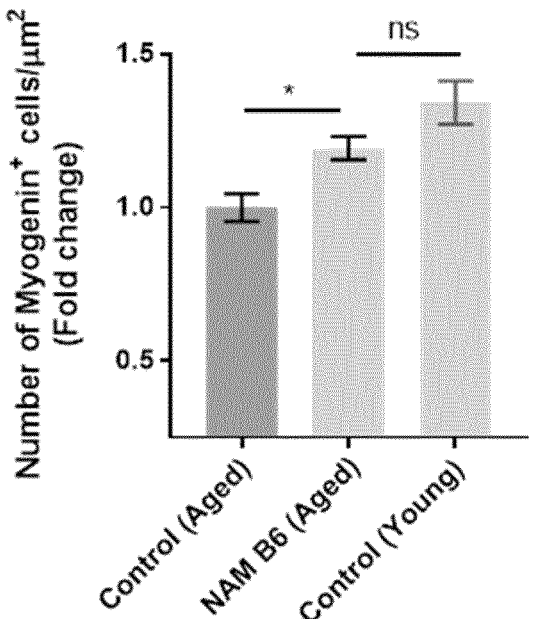
Figure 8:
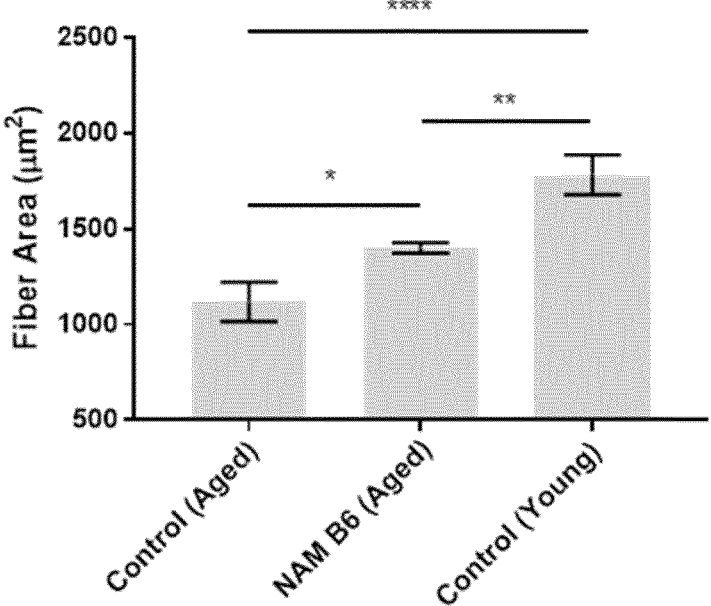

FIGS. 6-8: In vivo effect of the combination of nicotinamide (NAM) and pyridoxine (B6) on muscle stem cells function in adult and aged animals In order to reproduce the physiological process of muscle regeneration that occurs in adult skeletal muscles in response to injury or disease, we performed an intramuscular injection of cardiotoxin into mouse hindlimb muscles. One week prior to the induction of the muscle injury, mice were given by oral gavage our compounds of interest (nicotinamide and pyridoxine at 200 and 4 mg/kg body weight, respectively) vs. water control. Mice were treated once a day until the end of the experiment. To evaluate the efficiency of the muscle regeneration, muscles that have been previously injured were harvested 5 days (FIGS. 6 and 7) and 12 days (FIG. 8) after the injury and cryosections were prepared. Several myogenic markers were then measured. Cryosections were stained for Pax7, Myogenin, laminin (to delineate myofibers) and embryonic Myosin Heavy Chain (to define the injured/regenerating area) expression using specific antibodies and counterstained with Hoechst 33342 to visualize cell nuclei.

FIG. 6 represents early phase of expansion and subsequent phase of myogenic differentiation of Muscle Stem Cells in 3 months old mice defined as an adult population, evaluated by counting the number of Pax7+ cells (FIG. 6A) and Myogenin+ cells (FIG. 6B), respectively. Data are expressed as number of cells per arear of injured muscle and expressed as a fold change compared to the control condition. *, , *, **** indicates difference from the control, One-way ANOVA, with p<0.05, p<0.01, p<0.001, p<0.0001, respectively. Data are presented as Mean+/−SEM.

FIG. 7 represents early phase of expansion and subsequent phase of myogenic differentiation of Muscle Stem Cells, evaluated by counting the number of Pax7+ cells (FIG. 7A) and Myogenin+ cells (FIG. 7B), respectively performed in 24 months old mice defined as an aged population, as well as with "adult" mice as a control. Data are expressed as number of cells per arear of injured muscle and expressed as a fold change compared to the control condition. *, , *, **** indicates difference from the control, One-way ANOVA, with p<0.05, p<0.01, p<0.001, p<0.0001, respectively. Data are presented as Mean+/−SEM.

FIG. 8 represents late phase of muscle fiber maturation in 24 months old mice defined as an aged population, as well as with "adult" mice as a control evaluated by quantifying the size of each newly formed muscle fiber that has been measured based on the expression of the embryonic Myosin Heavy Chain and laminin that allow to recognize and delineate these nascent myofibers. Results are shown as mean muscle fiber cross-sectional area (µm2). *, , *, **** indicates difference from the control, One-way ANOVA, with p<0.05, p<0.01, p<0.001, p<0.0001, respectively. Data are presented as Mean+/−SEM.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

A "subject" or "individual" is a mammal, preferably a human. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "unit dosage form," as used herein, refers to physically discrete units suitable as unitary dosages for human and animal subjects, each unit containing a predetermined quantity of the composition disclosed herein in an amount sufficient to produce the desired effect, in association with a therapeutically effective diluent, carrier or vehicle. The specifications for the unit dosage form depend on the particular compounds employed, the effect to be achieved, and the pharmacodynamics associated with each compound in the host.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

The term "substantially no" as used in reference to a particular component means that any of the component present constitutes less than about 2.0% by weight, such as less than about 1.0% by weight, preferably less than about 0.5% by weight or, more preferably, less than about 0.1% by weight.

The term "food for special medical purpose (FSMP)" refers to formula foods specially processed and prepared in order to meet special needs for nutrient or diet of those suffering from food intake restriction, disorder of digestive absorption, disorder of metabolic or certain diseases. Such foods shall be used alone or together with other foods under the guidance of a doctor or clinical nutritionist. FSMP is special dietary food, not medicine, but not ordinarily eaten by normal people. It is specially developed by clinicians and nutritionists based on scientific facts after extensive medical research.

The term "oral nutritional supplement (ONS)" refers to sterile liquids, semi-solids or powders, which provide macro and micronutrients. They are widely used within the acute and community health settings for individuals who are unable to meet their nutritional requirements through oral diet alone.

As used herein, "vitamin B6" can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP.[2] Pyridoxine 5'-phosphate oxidase is dependent on flavin mononucleotide (FMN) as a cofactor produced from riboflavin (vitamin B2).

The term "elderly" in the context of a human means an age from birth of at least 60 years, preferably above 63 years, more preferably above 65 years, and most preferably above 70 years. In the context of non-human animals, "elderly" means a non-human subject that has reached 60% of its likely lifespan, in some embodiments at least 70%, at least 80% or at least 90% of its likely lifespan. A determination of lifespan may be based on actuarial tables, calculations, or estimates, and may consider past, present, and future influences or factors that are known to positively or negatively affect lifespan. Consideration of species, gender, size, genetic factors, environmental factors and stressors, present and past health status, past and present nutritional status, and stressors may be taken into consideration when determining lifespan.

The term "older adult" in the context of a human means an age from birth of at least 45 years, preferably above 50 years, more preferably above 55 years, and includes elderly individuals.

"Mobility" is the ability to move independently and safely from one place to another.

As used herein, Sarcopenia is characterized by one or more of low muscle mass, low muscle strength, and low physical performance. More preferably, sarcopenia is characterized by two or more of low muscle mass, low muscle strength, and low physical performance. Most preferably, sarcopenia is characterized by low muscle mass, low muscle strength, and low physical performance. These can all be measured by methods well known to the person skilled in the art.

Muscle mass can be measured by CT (computerised tomography), DXA (Dual-energy X-ray absorptiometry), MRI (Magnetic Resonance Imaging) or D3 creatine dilution methods.

Muscle strength can be measured by handgrip strength (for example, using handheld dynamometry) or knee extensor strength (for example, using quadriceps torque measurement).

Physical performance can be measured by gait speed, SPPB, 400 m walk test, time up and go test, or stair climbing test.

Sarcopenia can be diagnosed in a subject based on the definition of the AWGSOP (Asian Working Group for Sarcopenia in Older People), for example as described in Chen, et al. (2014) "Sarcopenia in Asia: consensus report of the Asian Working Group for Sarcopenia" Journal of the American Medical Directors Association 15, 95-101. Low muscle mass can generally be based on low appendicular lean mass normalized to height square (ALM index), particularly ALM index less than 7.00 kg/m2 for men and 5.40 kg/m2 for women. Low physical performance can generally be based on gait speed, particularly gait speed of <0.8 m/sec. Low muscle strength can generally be based on low hand grip strength, particularly hand grip strength less than 26 kg in men and less than 18 kg in women.

Sarcopenia can be diagnosed in a subject based on the definition of the EWGSOP (European Working Group for Sarcopenia in Older People), for example as described in Cruz-Jentoft et al., 2010 "Sarcopenia: European consensus on definition and diagnosis: Report of the European Working Group on Sarcopenia in Older People" Age Ageing 39, 412-423. Low muscle mass can generally be based on low appendicular lean mass normalized to height square (ALM index), particularly ALM index less than 7.23 kg/m2 for men and 5.67 kg/m2 for women. Low physical performance can generally be based on gait speed, particularly gait speed of <0.8 m/sec. Low muscle strength can generally be based on low hand grip strength, particularly hand grip strength less than 30 kg in men and less than 20 kg in women.

Sarcopenia can be diagnosed in a subject based on the definition of the Foundation for the National Institutes of Health (FNIH), for example as described in Studenski et al., 2014 "The FNIH sarcopenia project: rationale, study description, conference recommendations, and final estimates, J Gerontol A Biol Sci Med Sci. 69(5), 547-558. Low muscle mass can generally be based on low appendicular lean mass (ALM) normalized to body mass index (BMI; kg/m2), particularly ALM to BMI less than 0.789 for men and 0.512 for women. Low physical performance can generally be based on gait speed, particularly gait speed of <0.8 m/sec. Low muscle strength can generally be based on low hand grip strength, particularly hand grip strength less than 26 kg in men and less than 16 kg in women. Low muscle strength can also generally be based on low hand grip strength to body mass index, particularly hand grip strength to body mass index less than 1.00 in men and less than 0.56 in women.

The D3-creatine dilution method is another approach to measure muscle mass. This method is becoming more widely accepted as a robust standard and potentially a future alternative to DXA. The D3-creatine dilution method has been described previously e.g. in Clark et al. (2014) "Total body skeletal muscle mass: estimation by creatine (methyl-d3) dilution in humans" J Appl Physiol (1985). 2014 Jun. 15; 116(12):1605-13 and Stimpson et al. (2013) "Longitudinal changes in total body creatine pool size and skeletal muscle mass using the D3-creatine dilution method" J Cachexia Sarcopenia Muscle. June 25.

Embodiments

An aspect of the present disclosure is a composition comprising Nicotinamide and Vitamin B6. The composition comprising the Nicotinamide and Vitamin B6 is advantageous in preventing and/or treating the loss of and/or improving skeletal muscle mass, skeleton lean muscle mass, skeletal muscle strength and/or skeletal muscle function for a variety of reasons such as aging and inactivity due to injuries or sickness, for example for treating sarcopenia and/or physical frailty in an elderly adult.

Composition

Nicotinamide

Nicotinamide, also known as niacinamide or nicotinic acid amide, is the water-soluble, active form of vitamin B3.

The nicotinamide can be administered in an amount of about 0.001 mg/day to about 3000 mg/day, for example 1 mg/day to about 3000 mg/day, preferably about 10 mg/day to about 2000 mg/day, more preferably from 500 mg/day to about 1000 mg/day. Of course, the daily dose can be administered in portions at various hours of the day. However, in any given case, the amount of compound administered will depend on such factors as the solubility of the active component, the formulation used, subject condition (such as weight), and/or the route of administration. For example, the daily doses of nicotinamide disclosed above are non-limiting and, in some embodiments, may be different; in particular, the compositions disclosed herein can be utilized as an acute care food for special medical purposes (FSMP) and contain up to about 3.0 g nicotinamide/day.

Pyridoxine

Pyridoxine is the 4-methanol form of vitamin B6, an important water-soluble vitamin that is naturally present in many foods.

In an embodiment, vitamin B6 can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP. [2] Pyridoxine 5'-phosphate oxidase is dependent on flavin mononucleotide (FMN) as a cofactor produced from riboflavin (vitamin B2).

In an embodiment, Vitamin B6 can be administered in an amount of vitamin B6 in a daily dosage of about 1.0-600 mg vitamin B6, for example about 1.0-200 mg vitamin B6, for example about 1.0-25.0 mg vitamin B6, for example about 10-20 mg of Vitamin B6/day. In an embodiment, the combination is particularly effective, in particular on both amplification and commitment of muscle cells, when the pyridoxine: Nicotinamide are present in a ratio of from about 1:100 to about 1:9, preferably from about 1:80 to about 1:20, preferably from about 1:75 to about 1:25, more preferably from about 1:60 to about 1:30. In one embodiment, the pyridoxine:Nicotinamide are present in a ratio of from about 1:45 to about 1:30.

In some embodiments, the composition comprising a combination of the Nicotinamide and Vitamin B6 is in the form of a nutritional composition.

In some embodiments, the composition comprising a combination of the Nicotinamide and Vitamin B6 is in the form of a food product, food supplement, nutraceutical, food for special medical purpose (FSMP), nutritional supplement, dairy-based drink, low-volume liquid supplement or meal replacement beverage.

In some embodiments, the composition comprising a combination of the Nicotinamide and Vitamin B6 is in the form of a food additive or a medicament.

A food additive or a medicament may be in the form of tablets, capsules, pastilles or a liquid for example. Food additives or medicaments are preferably provided as sustained release formulations, allowing a constant supply of the active ingredients for prolonged times.

The composition may be selected from the group consisting of milk-powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; tablets; and/or syrups.

The composition may further contain protective hydrocolloids (such as gums, proteins, modified starches), binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and anti-microbials.

Further, the composition may contain an organic or inorganic carrier material suitable for oral or enteral administration as well as vitamins, minerals trace elements and other micronutrients in accordance with the recommendations of government bodies such as the USRDA.

The composition of the invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein and pea protein); mixtures of free amino acids; or combinations thereof. Milk proteins such as casein and whey, and soy proteins are particularly preferred.

If the composition includes a fat source, the fat source preferably provides 5% to 40% of the energy of the formula; for example, 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins and mixtures thereof.

Another aspect of the present disclosure is a kit comprising a therapeutically effective amount of any of the compositions disclosed herein. In an embodiment, the kit is configured for oral administration of the composition. For example, the kit can be in a form of two capsules, wherein the first capsule comprises the vitamin B6 and the second capsule comprises the Nicotinamide.

Another aspect of the present disclosure is a method of preparing the composition. The method can comprise combining a therapeutically effective amount of a combination of Nicotinamide and Vitamin B6, preferably an amount of the combination that is therapeutically effective for at least one of the physiological benefits disclosed herein.

Method of Treatment

It is to be appreciated that all references herein to treatment include curative, palliative and prophylactic treatment. The treatment of mammals, particularly humans, is preferred. Both human and veterinary treatments are within the scope of the invention.

In an embodiment, the present invention provides a method of preventing and/or treating a loss of and/or improving skeletal muscle mass, skeleton lean muscle mass, skeletal muscle grip strength and/or skeletal muscle function. The method comprises administering to an individual in need thereof a therapeutically effective amount of any of the compositions disclosed herein. Non-limiting examples of the administration include oral administration and intravenous administration. In an embodiment, the administration is oral administration. In an embodiment, the method comprises administering to an individual in need thereof a therapeutically effective amount of a combination of vitamin B6 and Nicotinamide.

In another embodiment, the method comprises administering to an individual in need thereof a therapeutically effective amount of a combination of an effective amount of vitamin B6 and Nicotinamide.

Although the composition for use in the invention can be administered alone, they will generally be administered in admixture with a pharmaceutical carrier, excipient or diluent, particularly for human therapy.

In a further embodiment of the invention, a compound or a composition of the invention may be used in a method of preventing and/or treating a loss of and/or improving skeletal muscle mass, skeleton lean muscle mass, skeletal muscle grip strength and/or skeletal muscle function in combination with a dietary intervention of high caloric, high protein, high carbohydrate, Vitamin B12 and/or Vitamin D supplementation, antioxidants, omega fatty acids, butyrate producers and/or polyphenols.

Within the context of the present invention, the expression "butyrate producer" indicate a substance or ingredient which, when administered to a subject, is able to deliver and/or stimulate the production of butyrate, for example in the gut of said subject. Not limiting examples of butyrate producers are: sodium butyrate, potassium butyrate and/or triglycerides containing butyrate such as for example those described in the patent application WO 2019/228851 of the same applicant.

In some embodiments, the composition comprising a combination of the Nicotinamide and Vitamin B6 is in a combined preparation for simultaneous, separate or sequential use, preferably simultaneous.

The term "combination", or terms "in combination", "used in combination with" or "combined preparation" as used herein may refer to the combined administration of two or more agents simultaneously, sequentially or separately.

The term "simultaneous" as used herein means that the agents are administered concurrently, i.e. at the same time.

The term "sequential" as used herein means that the agents are administered one after the other.

The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

In an embodiment, the method comprises administering to an individual in need thereof a therapeutically effective amount of a combination of vitamin B6 in a daily dosage of 1.0-600 mg vitamin B6 per day, preferably 1.0-200 mg vitamin B6 per day, preferably 1.0-25.0 mg vitamin B6 per day and Nicotinamide in an amount of about 1 mg/day to about 3000 mg/day, preferably about 10 mg/day to about 2000 mg/day, more preferably from 500 mg/day to about 1000 mg/day.

In an embodiment, the combination is administered to the individual for a time period of at least one month; preferably at least two months, more preferably at least three, four, five or six months; most preferably for at least one year. During the time period, the combination can be administered to the individual at least one day per week; preferably at least two days per week, more preferably at least three, four, five or six days per week; most preferably seven days per week. The combination can be administered in a single dose per day or in multiple separate doses per day.

The above examples of administration do not require continuous daily administration with no interruptions. Instead, there may be some short breaks in the administration, such as a break of two to four days during the period of administration. The ideal duration of the administration of the composition can be determined by those of skill in the art.

Subject

In some embodiments, a subject is a human or non-human animal.

Examples of non-human animals include vertebrates, for example mammals, such as non-human primates (particu-larly higher primates), dogs, rodents (e.g. mice, rats or guinea pigs), pigs and cats. The non-human animal may be a companion animal.

Preferably, the subject is a human.

In an embodiment, the individual is selected from the group consisting of an aging subject; an elderly subject; a subject with muscle fatigue or muscle weakness; a subject with impaired mobility; a frail subject; a pre-frail subject; a sarcopenic subject; a subject recovering from pre-frailty, frailty, sarcopenia or impaired mobility; a subject undergoing physical rehabilitation (e.g., from an injury to one or more of a muscle, a bone, a ligament, or the nervous system); a sportsman; and a pet.

Preferably, the muscle functionality that can be improved by the methods disclosed herein comprises a characteristic selected from the group consisting of muscle strength, gait speed, and combinations thereof. Muscle function is typically defined as strength per unit of appendicular skeletal muscle mass or per muscle volume.

Non-limiting examples of a muscle disorder linked to calcium depletion or deficiency that can be treated by the methods disclosed herein include muscular dystrophies, congenital core myopathies and mitochondrial myopathies. Particular non-limiting examples include Barth syndrome; chronic progressive external ophthalmoplegia (cPEO); Kearns-Sayre syndrome (KSS); Leigh syndrome; mitochondrial DNA depletion syndromes (MDDS); mitochondrial encephalomyopathy, lactic acidosis, and stroke-like episodes (MELAS); mitochondrial neurogastrointestinal encephalomyopathy (MNGIE); myoclonus epilepsy with ragged red fibers (MERRF); neuropathy, ataxia, and retinitis pigmentosa (NARP); and Pearson syndrome.

The individual can be at risk of a disorder or condition (e.g., sarcopenia, frailty, muscle fatigue or muscle weakness, or impairment in one or more of muscle functionality, muscle performance, or muscle strength), in which case the effective amount of the composition is a prophylactically effective dose; or the individual can have a disorder or condition, in which case the effective amount of the composition is a therapeutically effective dose. In some embodiments, the methods comprise identifying the individual as having the condition or being at risk of the condition before the administration.

In another embodiment, the present disclosure provides a method of treating or preventing impaired mobility in an older adult. The method comprises orally administering to the older adult an effective amount of a combination of calcium and at least one of oleuropein or metabolite thereof. The older adult can be an elderly individual. In some embodiments, the older adult has a condition selected from the group consisting of frailty, pre-frailty, sarcopenia, recovering from sarcopenia, osteoporosis, osteoarthritis, malnutrition, at risk of malnutrition, undergoing rehabilitation, scheduled to undergo rehabilitation within the next year, and combinations thereof.

The composition may be administered to the older adult in an amount sufficient to prevent, at least partially reduce the risk of developing frailty or sarcopenia, and/or at least partially reduce the severity of pre-frailty, frailty, sarcopenia or impaired mobility in instances where the condition has yet not been developed in the individual. Such an amount is defined to be "a prophylactically effective dose." Again, the precise amounts depend on a number of factors relating to the individual, such as their weight, health and how much muscle functionality (e.g., muscle strength, gait speed, etc.) is being lost.

EXAMPLES

The following non-limiting examples support the unexpected effectiveness of a composition comprising Nicotinamide and vitamin B6 for preventing and/or treating the loss of skeletal muscle mass, muscle strength and/or muscle function.

Example 1 Myogenic Amplification and Commitment of Muscle Stem Cells

Material and Methods

Human primary myoblasts from different donors (donor 1, donor 2 or donor 3) were seeded in 384 well plates at a density of 1'000 cells per well in skeletal muscle growth medium (SKM-M, AMSbio). For treatment, compounds were directly added to the myoblast cultures 16 hours after initial plating.

All cultures were then grown for 96 hours. Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification.

Additionally, several ratios between Pyridoxine and Nicotinamide (ratio Vitamin B6/NAM) ranging from 1:2 to 1:80 were tested and FIG. 8 represents the number of Pax7+ cells for these specific ratios in the same model.

*, , *, **** indicates difference from the control, One-way ANOVA, with $p<0.05$, $p<0.01$, $p<0.001$, $p<0.0001$, respectively. Data are presented as Mean+/−SEM Results Results are presented in FIGS. 1 to 5.

Data obtained from Human primary myoblasts from donors 1 and 2 were pooled (see FIG. 1). For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 1A represents the proportion of Pax7+ cells and FIG. 1B represents the proportion of MyoD+ cells. These data demonstrate that Nicotinamide promotes Muscle Stem Cell function by increasing the proportion of both amplifying (Pax7+) and differentiating (MyoD+) cells in a dose dependent manner.

Similarly, for Pyridoxine, data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 2A represents the proportion of Pax7+ cells and FIG. 2B represents the proportion of MyoD+ cells. These data demonstrate that Pyridoxine promotes Muscle Stem Cell function by increasing the proportion of differentiating (MyoD+) cells in a dose dependent manner.

FIG. 3 represents the effect of nicotinamide and pyridoxine alone or combined on MyoD+ cells (from donor 3). For each condition, the number of MyoD+ cells was normalized to the number of MyoD+ cells in the control condition (DMSO 1%). FIG. 3A represents the number of MyoD+ cells normalized to the control condition. FIG. 3B represents the increase in MyoD+ cell number compared to the control condition (DMSO 1%). These data show that the effect of the combination of Nicotinamide and Pyridoxine is greater than the sum of the individual effect of Nicotinamide and Pyridoxine, indicating a synergistic effect. Indeed, by applying a linear regression model (interaction term, $p=0.05$), we were able to observe a statistically significant synergistic effect between the nicotinamide and pyridoxine.

As a comparative experiment, combination of Nicotinamide (NAM) with vitamin B9 was measured similarly as above (see FIG. 4). Unlike pyridoxine (vitamin B6), vitamin B9, another member of the B vitamin complex, does not have any addictive nor synergistic effect when added in combination with Nicotinamide. Additionally, FIG. 5 demonstrates that the ratio between Pyridoxine and Nicotinamide (ratio Vitamin B6/NAM) has a relevant impact on promoting muscle stem cell function.

Example 2 In Vivo Effect of the Combination of Nicotinamide (NAM) and Pyridoxine (B6) on Muscle Stem Cells Function in Adult and Aged Animals Material and Methods In order to reproduce the physiological process of muscle regeneration that occurs in adult skeletal muscles in response to injury or disease, we performed an intramuscular injection of cardiotoxin into mouse hindlimb muscles. One week prior to the induction of the muscle injury, mice were given by oral gavage our compounds of interest (nicotinamide and pyridoxine at 200 and 4 mg/kg body weight, respectively) vs. water control. Mice were treated once a day until the end of the experiment. To evaluate the efficiency of the muscle regeneration, muscles that have been previously injured were harvested 5 days (FIGS. 6 and 7) and 12 days (FIG. 8) after the injury and cryosections were prepared. Several myogenic markers were then measured. Cryosections were stained for Pax7, Myogenin, laminin (to delineate myofibers) and embryonic Myosin Heavy Chain (to define the injured/regenerating area) expression using specific antibodies and counterstained with Hoechst 33342 to visualize cell nuclei. Early phase of expansion and subsequent phase of myogenic differentiation of Muscle Stem Cells were evaluated by counting the number of Pax7+ cells (FIG. 6A and FIG. 7A) and Myogenin+ cells (FIG. 6B and FIG. 7B), respectively. Data are expressed as number of cells per arear of injured muscle, expressed as a fold change compared to the control condition. Late phase of muscle fiber maturation (FIG. 8) was evaluated by quantifying the size of each newly formed muscle fiber that has been measured based on the expression of the embryonic Myosin Heavy Chain and laminin that allow to recognize and delineate these nascent myofibers. Results are shown as muscle fiber cross-sectional area (µm2). Experiments shown in FIG. 6 were performed with 3 months old mice defined as an adult population. Experiments shown in FIGS. 7 and 8 were performed with 24 months old mice defined as an aged population, as well as with "adult" mice as a control.

Results

These data demonstrate that a combination of Nicotinamide and Pyridoxine promotes Muscle Stem Cell function by increasing the number of both amplifying (Pax7+) and differentiating (MyoD+) cells in an in vivo preclinical model of muscle repair/regeneration (FIG. 6). Similar experiments were also performed in aged animals (FIG. 7) and demonstrate that also in the context of aging, a combination of Nicotinamide and Pyridoxine promotes Muscle Stem Cell function by increasing the number of both amplifying (Pax7+) and differentiating (MyoD+) cells, restoring these biological readouts to the levels of the adult animals. Additionally, FIG. 8 demonstrates that a combination of Nicotinamide and Pyridoxine is able to promote the muscle repair process by increasing the size of the newly formed muscle fibers.

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for treating sarcopenia and/or physical frailty, and/or improving skeletal muscle mass, skeletal muscle lean mass, skeletal muscle strength and/or skeletal muscle function in an individual in need thereof, the method comprising administering to the individual a therapeutically effective amount of a composition comprising a combination of Vitamin B6 and Nicotinamide in a weight ratio of from about 1:80 to about 1:20.

2. The method according to claim 1, wherein the Vitamin B6 is administered in an amount of 1.0-600 mg vitamin B6 per day.

3. The method according to claim 1, wherein the Nicotinamide is administered in an amount of about 1 mg/day to about 3000 mg/day.

4. The method according to claim 1, wherein the Vitamin B6 is administered in an amount of 10-20.0 mg vitamin B6 per day, and the Nicotinamide is administered in an amount of about 500 mg to about 1000 mg Nicotinamide per day.

5. The method according to claim 1, wherein the Vitamin B6: Nicotinamide are present in a weight ratio of from about 1:100-60 to about 1:930.

6. The method according to claim 1, wherein the Vitamin B6: Nicotinamide are present in a weight ratio of from about 1:45 to about 1:30.

7. The method according to claim 1, wherein the composition is in a form selected from the group consisting of an oral nutritional composition, a nutritional supplement, an oral nutritional supplement, a medical food, a food supplement, a food product, and a food for special medical purpose (FSMP).

8. The method according to claim 1, wherein the composition is in a form selected from the group consisting of a solid powder, a powdered stick, a capsule and a solution.

9. The method according to claim 1, wherein the individual has sarcopenia or is at risk thereof, and the administering of the therapeutically effective amount of the composition restores and/or corrects deficiencies of nutrients in the individual.

10. The method according to claim 1, wherein the individual is selected from the group consisting of an aging subject; an elderly subject; a subject with muscle fatigue or muscle weakness; a subject with impaired mobility; a frail subject; a pre-frail subject; a sarcopenic subject; and a subject recovering from pre-frailty, frailty, sarcopenia and impaired mobility.

11. The method according to claim 1, wherein the composition is a food product further comprising a component selected from the group consisting of protein, carbohydrate, fat and mixtures thereof.

12. The method according to claim 1, wherein the administering of the therapeutically effective amount of the composition treats sarcopenia in the individual.

13. The method according to claim 1, wherein the administering of the therapeutically effective amount of the composition treats physical frailty in the individual.

14. The method according to claim 1, the administering of the therapeutically effective amount of the composition improves skeletal muscle mass, skeletal muscle lean mass, skeletal muscle strength and/or skeletal muscle function in the individual.

15. The method according to claim 1, wherein the Vitamin B6 is administered in an amount of 10-20.0 mg vitamin B6 per day.

16. The method according to claim 1, wherein the Nicotinamide is administered in an amount of about 500 mg to about 1000 mg Nicotinamide per day.

* * * * *